United States Patent
Visser et al.

(10) Patent No.: US 10,473,526 B2
(45) Date of Patent: Nov. 12, 2019

(54) SPATIALLY RESOLVED GAS DETECTION

(71) Applicant: Nederlandse Organisatie voor toegepast-natuurwetenschappelijk onderzoek TNO, The Hague (NL)

(72) Inventors: Huibert Visser, The Hague (NL); Hedser van Brug, The Hague (NL)

(73) Assignee: NEDERLANDSE ORGANISATIE VOOR TOEGEPAST-NATUURWETENSCHAPPELIJK ONDERZOEK TNO, The Hague (NL)

( * ) Notice: Subject to any disclaimer, the term of this patent is extended or adjusted under 35 U.S.C. 154(b) by 15 days.

(21) Appl. No.: 15/526,816

(22) PCT Filed: Nov. 13, 2015

(86) PCT No.: PCT/NL2015/050799
§ 371 (c)(1),
(2) Date: May 15, 2017

(87) PCT Pub. No.: WO2016/076724
PCT Pub. Date: May 19, 2016

(65) Prior Publication Data
US 2018/0283949 A1    Oct. 4, 2018

(30) Foreign Application Priority Data

Nov. 13, 2014    (EP) .................................... 14192989

(51) Int. Cl.
*G01J 3/45*    (2006.01)
*G01J 3/36*    (2006.01)
(Continued)

(52) U.S. Cl.
CPC . *G01J 3/45* (2013.01); *G01J 3/36* (2013.01); *G01J 3/42* (2013.01); *G01J 3/447* (2013.01);
(Continued)

(58) Field of Classification Search
CPC .......... G01J 3/45; G01J 3/4531; G01J 3/4532; G01J 3/36; G01J 3/42; G01J 3/447;
(Continued)

(56) References Cited

U.S. PATENT DOCUMENTS 5,910,838 A  *  6/1999  Weisse ............... G01N 21/3103
                                                     356/307
5,982,497 A     11/1999  Hopkins
(Continued)

FOREIGN PATENT DOCUMENTS

FR           2787186 A1      6/2000
WO        2006113996 A1     11/2006
(Continued)

OTHER PUBLICATIONS

Georgieva, Elena M., William S. Heaps, and Emily L. Wilson. "Differential radiometers using Fabry-Perot interferometric technique for remote sensing of greenhouse gases." IEEE Transactions on Geoscience and Remote Sensing 46.10 (2008): 3115-3122.
(Continued)

*Primary Examiner* — Tarifur R Chowdhury
*Assistant Examiner* — Jonathon Cook
(74) *Attorney, Agent, or Firm* — Hoffmann & Baron, LLP (57) ABSTRACT

The invention pertains to a method of spatially resolved detection of a gas substance in an area, comprising: imaging the area on a first image sensor, in a wavelength spectrum including an absorption wavelength peak corresponding to said gas substance; imaging the area on a second image sensor, to provide for each pixel of the first image a corresponding pixel of the second image for respective on- and off-peak wavelengths relative to the absorption wavelength; and providing a difference image as a function of the two pixel values of first and second image sensors to produce an image of the spatially resolved absorption wavelength corresponding to said gas substance.

8 Claims, 11 Drawing Sheets

(51) Int. Cl.
*G01J 3/42* (2006.01)
*G01J 3/447* (2006.01)
*G01J 3/453* (2006.01)
*G01N 21/31* (2006.01)
*G01N 21/39* (2006.01)
*G01N 33/00* (2006.01)

(52) U.S. Cl.
CPC ........... *G01J 3/4531* (2013.01); *G01J 3/4532* (2013.01); *G01N 21/31* (2013.01); *G01N 21/314* (2013.01); *G01N 21/39* (2013.01); *G01N 33/0027* (2013.01)

(58) Field of Classification Search
CPC ...... G01N 21/31; G01N 21/314; G01N 21/39; G01N 33/0027
USPC .................................................. 356/451, 453
See application file for complete search history.

(56) References Cited

U.S. PATENT DOCUMENTS

| | | | |
|---|---|---|---|
| 2002/0081013 A1* | 6/2002 | Raz | G06K 9/0014 382/133 |
| 2007/0018103 A1* | 1/2007 | DeCamp | G01J 3/4338 250/339.06 |
| 2007/0152154 A1* | 7/2007 | DeCamp | G01J 3/2803 250/339.07 |
| 2008/0198365 A1* | 8/2008 | Treado | G01J 3/02 356/73 |
| 2009/0051899 A1 | 2/2009 | Harlander et al. | |
| 2012/0197137 A1* | 8/2012 | Jeanne | A61B 5/02028 600/479 |
| 2014/0125985 A1* | 5/2014 | Justice | G01J 3/0202 356/456 |
| 2014/0354873 A1* | 12/2014 | Parsons | G01J 3/0227 348/342 |

FOREIGN PATENT DOCUMENTS

| | | |
|---|---|---|
| WO | 2013010272 A1 | 1/2013 |
| WO | 2013173541 A1 | 11/2013 |

OTHER PUBLICATIONS

Brachet, Frank, et al. "Static Fourier transform spectroscopy breadboards for atmospheric chemistry and climate." Proc. SPIE. vol. 7100. No. 710019. 2008.

* cited by examiner

SPATIALLY RESOLVED GAS DETECTION

This application is the U.S. National Phase of, and Applicants claim priority from, International Patent Application Number PCT/NL2015/050799 filed 13 Nov. 2015, which claims priority from EP 14192989.3 filed 13 Nov. 2014, each of which is incorporated herein by reference.

FIELD OF THE INVENTION

The invention relates to a method and system for spatially resolved gas detection, in particular in a satellite application that orbits the planet.

BACKGROUND OF THE INVENTION

Remote sensing, i.e. the monitoring of particular gas molecules in the Earth's atmosphere, started with instruments having single element sensors in front of which a spectral band filter was placed, e.g. TOMS. In order to arrive at some sort of Earth coverage, a 1D scanner in swath direction was required. In flight direction the coverage was obtained by the relative velocity of the satellite with respect to the Earth surface. Later these single detectors were replaced by linear arrays. These were used in a similar way as the single cell detectors, except that no band filter was used. Instead of that, a spectrometer was employed to spread out the light over the number of pixels of the linear array. Finally, 2D sensors became available so that the swath scanner was no longer needed. The full swath is imaged onto a row of pixels while each ground pixel is spectrally dispersed in the orthogonal direction.

Satellites are orbiting the Earth at an altitude of typically between 400 and 800 km. These orbits are indicated as Low Earth Orbits (LEO). The speed of these satellites relative to the Earth is about 7 km/s. Since an integration time of about 1 s is needed to arrive at a good enough Signal to Noise Ratio (SNR), an effective ground pixel on Earth will be about 7 km in flight direction. Most often some binning in the swath direction is used leading to square ground pixels of e.g. 7×7 km.

The drawback of a spectrometer is that the intensity being measured is dispersed over many spectral detector pixels resulting in low signal levels per detector pixel.

Scientists are asking for smaller ground pixels while keeping good SNR values. This is virtually impossible since the scattering by the Earth is a constant, as is the output of the Sun, so the only way to decrease the ground pixel size is by moving towards larger entrance apertures and smaller f-numbers in the optical design. This leads to larger, heavier, and more expensive instruments.

SUMMARY OF THE INVENTION

The invention aims to overcome these problems by a method of spatially resolved detection of a gas substance in an area, comprising: imaging the area on a first image sensor, in a wavelength spectrum including an absorption wavelength peak corresponding to said gas substance; imaging the area on a second image sensor, to provide for each pixel of the first image a corresponding pixel of the second image for respective on- and off-peak wavelengths relative to the absorption wavelength; and providing a difference image as a function of the two pixel values of first and second image sensors to produce an image of the spatially resolved absorption strength relative to the concentration of said gas substance.

It is noted that from FR2787186A1 a stepped phase is provided in a modified interferometer of a Michaelson type. However in the novel gas detection method, smaller ground pixels can accordingly be obtained by using a camera instead of a spectrometer so that instantaneous wide image spatially resolved detection of a gas substance can be provided. In another aspect of the invention a gas detector system is provided for spatially resolved detection of a gas substance in an area, comprising a detector comprising first and second image sensors; a broad band filter arranged in the optical beam path before the detector; for transferring a broad band beam with a wavelength spectrum including an absorption wavelength peak corresponding to said gas substance; a telescope, splitter; and relay optics; wherein the telescope is arranged to imaging the area onto the image sensors; wherein the splitter is arranged to produce split images; and wherein said relay optics are arranged to receiving said split images respectively to produce first and second images on first and second image sensors; to provide for each pixel of the first image a corresponding pixel of the second image for respective on- and off-peak wavelengths relative to the absorption wavelength; and wherein a controller is coupled to the detector, arranged to provide a difference image as a function of the two pixel values of first and second image sensors to produce an image at the spatially resolved absorption wavelength corresponding to said gas substance.

In an embodiment, the information that is to be measured can be obtained by interferometry (for spectrally narrow absorption features) or by band filters (for wider absorption features). In yet another aspect of the invention a gas detector system is provided for spatially resolved detection of a gas substance in an area, comprising; a detector comprising first and second image sensors; a broad band filter arranged in the optical beam path before the detector; for transferring a broad band beam with a wavelength spectrum including an absorption wavelength corresponding to said gas substance; a telescope, splitter; and relay optics; wherein the telescope is arranged to imaging the area onto the image sensors; wherein the splitter is arranged to produce split images; and wherein said relay optics are arranged to receiving said split images respectively to produce first and second images on first and second image sensors; wherein a retarder is inserted before the splitter to image in order to create a phase difference between two orthogonally polarization components that is wavelength dependent, and wherein said relay optics comprise a polarizing beam splitter that combines said polarization components at exit ports to produce phase stepped images at different phases; and a controller coupled to the detector, arranged to provide a difference image as a function of the two pixel values of first and second image sensors to produce an image at the spatially resolved absorption wavelength corresponding to said gas substance.

BRIEF DESCRIPTION OF THE DRAWINGS

FIG. 1 (A, B, C) shows the absorption band O2A

DETAILED DESCRIPTION OF EMBODIMENTS

Unless otherwise defined, all terms (including technical and scientific terms) used herein have the same meaning as commonly understood by one of ordinary skill in the art to which this invention belongs as read in the context of the description and drawings. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some instances, detailed descriptions of well-known devices and methods may be omitted so as not to obscure the description of the present systems and methods. The term "and/or" includes any and all combinations of one or more of the associated listed items. It will be further understood that the terms "comprises" and/or "comprising" specify the presence of stated features but do not preclude the presence or addition of one or more other features. All publications, patent applications, patents, and other references mentioned herein are incorporated by reference in their entirety. In case of conflict, the present specification, including definitions, will control.

Throughout the application, any means for carrying out the disclosed methods, in particular, as further clarified below: means imaging, means for splitting, means for relaying can be implemented by optics that are known to the skilled person and may differ in form and structure to arrive at the same function; i.e. the function is physically implemented in optical elements such as mirrors, lenses and prisms. Furthermore, the identified controller functions may be implemented in hardware or software, to provide dedicated processing circuitry that processes input data read from system resources. A server function may e.g. be provided by a connected physical network device, but may also be formed as a virtual device, functioning in a network, and which may be implemented on a hardware resource that can be reached via network communication. These functions may be executed by one or more processors configured to perform operational acts in accordance with the present systems and methods, such as to provide control signals to the various other module components. The controller may comprise a processor that may be a dedicated processor for performing in accordance with the present system or may be a general-purpose processor wherein only one of many functions operates for performing in accordance with the present system. The processor may operate utilizing a program portion, multiple program segments, or may be a hardware device utilizing a dedicated or multi-purpose integrated circuit. Any type of processor may be used such as dedicated or shared one. The processor may include microcontrollers, central processing units (CPUs), digital signal processor s (DSPs), ASICs, or any other processor(s) or controller(s) such as digital optical devices, or analog electrical circuits that perform the same functions, and employ electronic techniques and architecture. The controller or processor may further comprise a memory that may be part of or operationally coupled to the controller. The memory may be any suitable type of memory where data is stored. Any medium known or developed that can store and/or transmit information suitable for use with the present systems and methods may be used as a memory. The memory may also store user preferences and/or application data accessible by the controller for configuring it to perform operational acts in accordance with the present systems and methods.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. The description of the exemplary embodiments is intended to be read in connection with the accompanying drawings, which are to be considered part of the entire written description. In the drawings, the size and relative sizes of systems, components, layers, and regions may be exaggerated for clarity. Embodiments are described with reference to schematic illustrations of possibly idealized and/or intermediate structures of the invention.

Figure 1A:
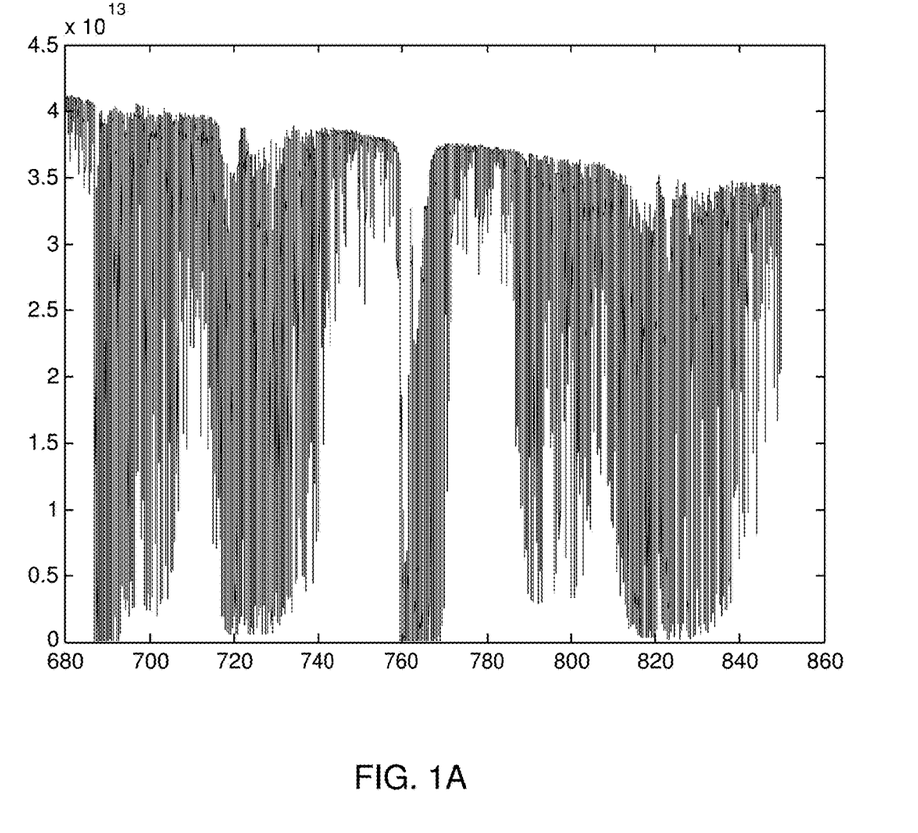
Figure 1B:
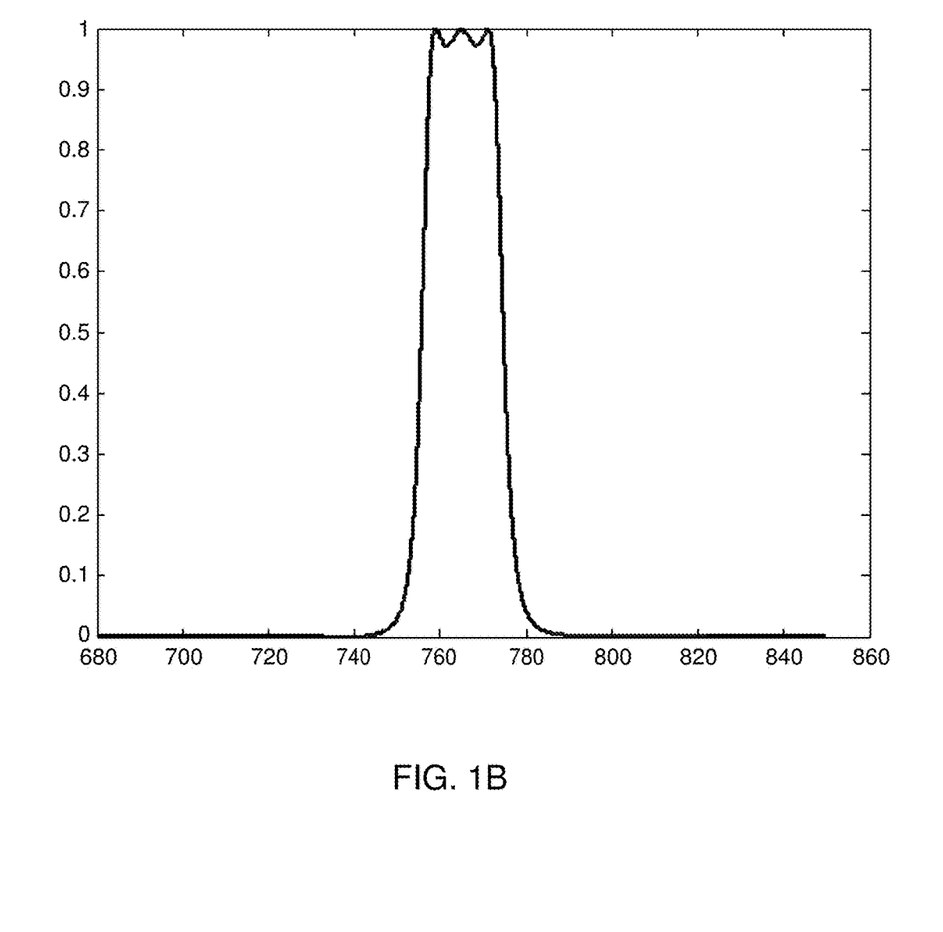
Figure 1C:
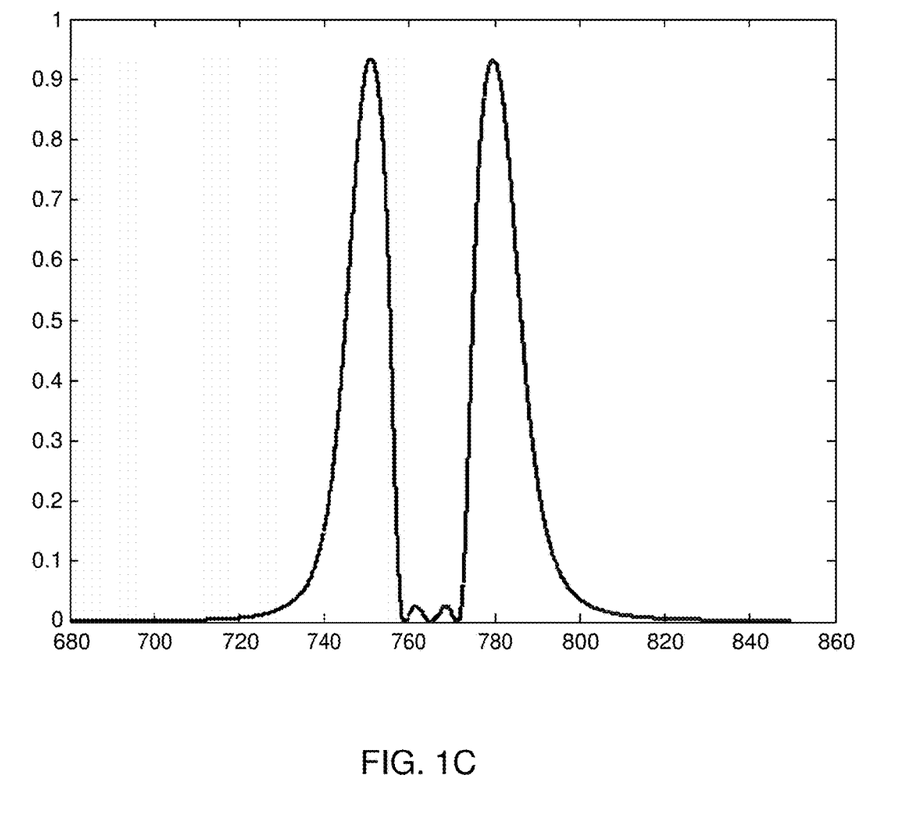
Figure 2:
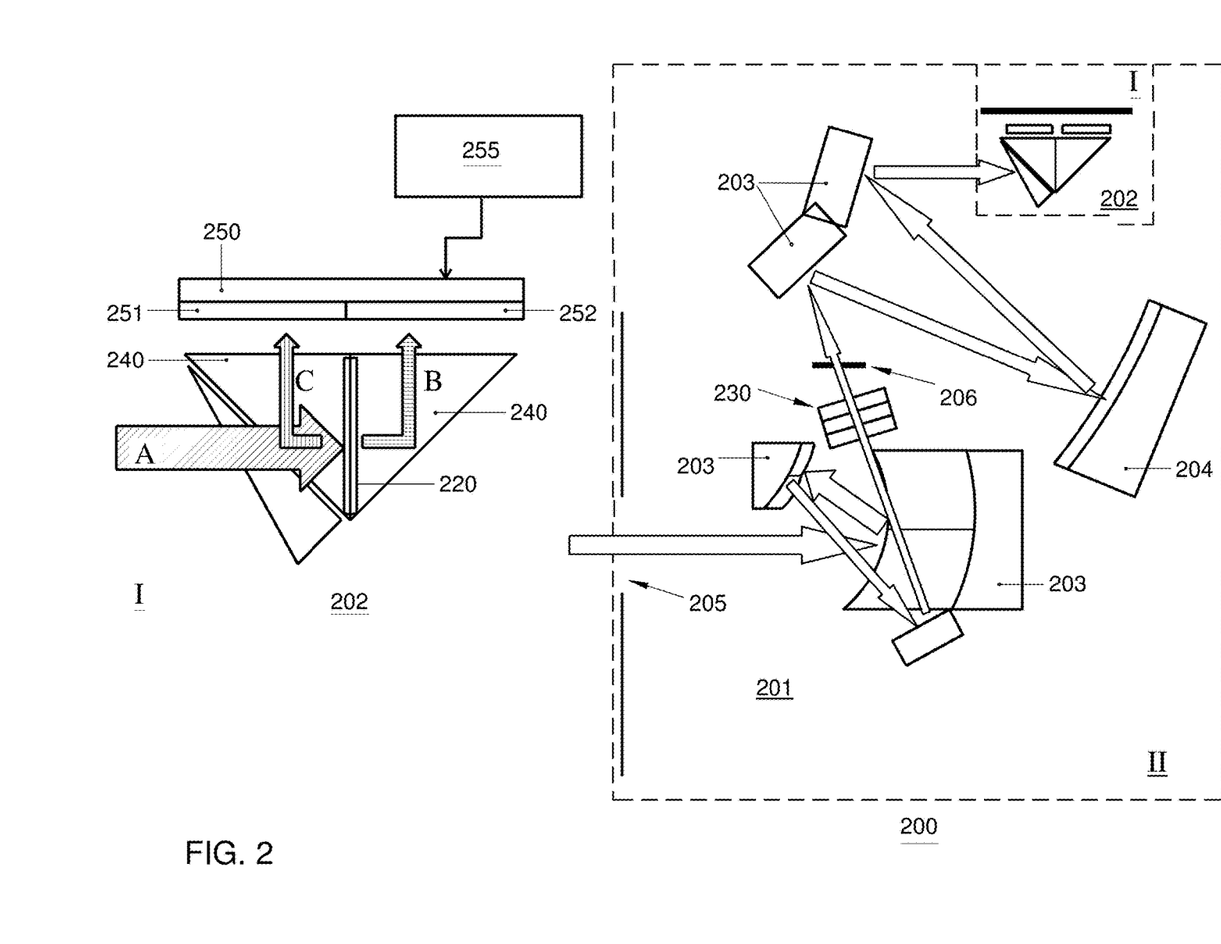
FIG. 2 shows a gas detector system for the absorption band of FIG. 1

Turning now to FIG. 1 in connection with FIG. 2, there is disclosed a gas detector that may function as a cloud detector (FIG. 2) by analyzing the absorption in the O2A band (FIG. 1A) at about 765 nm wavelength optimized to handle a field of view of 108×36°. For the O2A band, having a width that exceeds 10 nm, in particular, is about 20-30 nm, a wide band filter can be used to define a wide band in which the absorption feature occurs, and a narrow band filter that is located at the absorption feature itself. The narrow band filter measures the Earth signal at the spectral absorption feature while the broad band filter is used to measure the Earth signal of the wavelengths adjacent to the spectral absorption feature. The presented band filter design is meant for the O2A band at about 765 nm wavelength.

Table 1 presents some figures that are calculated by a controller coupled to the detector, to provide a difference image in the form of a Ratio and Visibility calculation for two pixel values of first and second image sensors to produce an image at the spatially resolved absorption wavelength corresponding to said gas substance.

|  | Ratio (Band/Side) | Visibility (Side − Band/Side + Band) |
|---|---|---|
| High Latitude Bright | 0.6365 | 0.2221 |
| High Latitude Dark | 0.6685 | 0.1987 |
| Tropical Bright | 0.6565 | 0.2074 |
| Tropical Dark | 0.6775 | 0.1922 |

This approach can be combined with an interferometric system as disclosed in the subsequent figures. In case the interferometer approach is not used a broad band filter can be used as pre filter while a narrow band filter is used to split the light between the two exit ports. In this way the sum of the two signals is the intensity of the full broad band spectrum.

Additionally it can be made such that it measures the intensity on both the low and high end of the spectrum. The splitter may in this case be a dichroic mirror. In front of the detector two narrow bands filters may be placed to define the wavelength bands seen per detector half.

FIG. 2 shows in detail the gas detector system 200 with in I the splitter section 202 and in II combined with a telescope section 201. In the FIG. 21 the splitter section 202 is formed by a broad band filter 230 that filters a wavelength between 720 and 820 nm, a narrow band filter 220 that splits the broad band beam into a narrow band (FIG. 1B) with a wavelength between 740 and 780 nm matching the O2A band of 765 nm and relay prisms 240, by transmitting or reflecting the narrow band, and reflecting or transmitting respectively the remaining spectral band. The narrow band filter 220 corresponds to the O2A absorption peak. A remaining spectral band beam (FIG. 1C) may be reflected from the narrow band filter 220, thereby functioning as a splitter to produce first and second images via relay prisms 240 onto first and second image sensors 251, 252 in a narrow band B and a remaining spectral band C respectively with a wavelength difference corresponding to on- and off-peak wavelengths relative to the absorption wavelength of 765 nm. Accordingly a gas detector system 200 is shown for spatially resolved detection of a gas substance in an area, comprising: a detector 250 comprising first and second image sensors 251, 252; a broad band filter 230 arranged in the optical beam path before the detector 250; for transferring a broad band beam with a wavelength spectrum A including an absorption wavelength peak B corresponding to said gas substance; a telescope 201, splitter 220; and relay optics 240; wherein the telescope 201 is arranged to imaging the area onto the image sensors 251; 252; wherein the splitter 220 is arranged to produce split beams B, C; and wherein said relay optics 240 are arranged to relay said split beams respectively to produce first B and second images C on first and second image sensors 251, 252. First and second images B and C are featured in such a way, that for each pixel of the first image B a corresponding pixel of the second image C is relayed for respective on- and off-peak wavelengths (B, resp. C) relative to the absorption wavelength, being the narrow band filter wavelength tuned to the absorption peak. Controller 255 is coupled to the detector 250, arranged to provide a difference image as a function of the two pixel values of first and second image sensors 251, 252 to produce an image at the spatially resolved absorption wavelength corresponding to said gas substance.

FIG. 2II schematically shows a telescope system 201 and ray paths for the gas detector 200. In the example the telescope 201 is geared to a Low Earth Orbit, with height typically between 400 and 800 km. For this height a Field of View can be chosen freely with a trade off between coverage and resolution. Advantageously full daily ground coverage can be obtained at an orbit height close to 800 km by an observation angle in swath direction of about ±54°. In flight direction the angle dictates the amount of time that a ground pixel is imaged onto the detector and is preferably as high as possible, for example from about ±18° to about more than 100 degrees to provide an optimal (maximum) intensity on the detector as the case may be. The shown design provides a wide view telecentric image, in particular to better than one tenth of a degree. In this exemplary embodiment the telescope unit 201 comprises four aspheric mirrors 203 with an even aspheric folding mirror 204, i.e. a central mirror. The apparent aperture 205 at the entrance is oversized since the actual system stop 206 is just after the broad band filter 230. Since the telescope system 201 is mirror based no colour aberration is present. Some measures may be taken to prevent the camera from saturation at an albedo of one. This may be done by bare aluminium 'poor reflection' mirrors. The telescope system is reflection based and is thereby inherently wavelength independent. Due to the insertion of the filter block and the splitter optics in front of the detector longitudinal colour is introduced. A stop 206 is arranged within the system, while the telescope images the stop at the entrance of the system. At this location an oversized diaphragm can be placed, thus reducing straylight and the pollution of the system.

Figure 3:
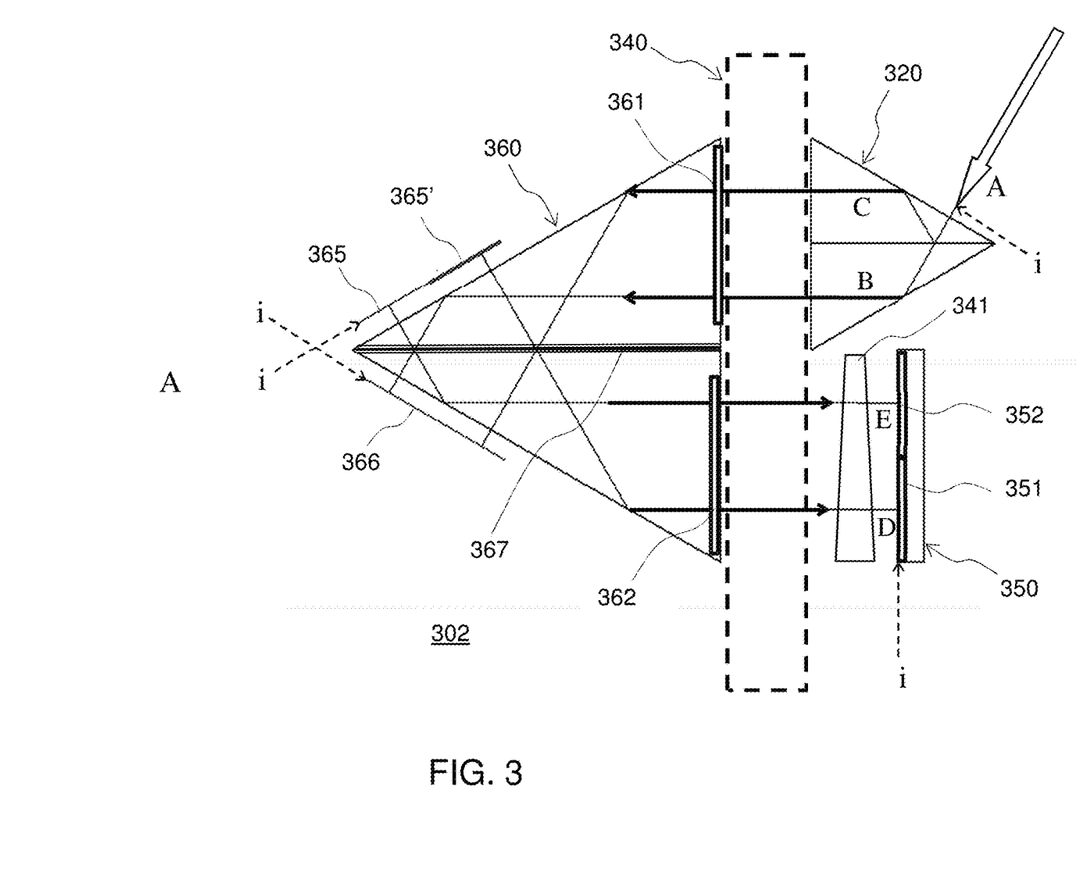
FIG. 3 schematically shows another design with an interferometer stage.

In FIG. 3, schematically, another design 302 is shown, wherein splitter 320 is combined with an interferometer stage 360. For this approach an angular independent Optical Path Difference (OPD) is created such that a spectral fringe pattern is created that coincides with the absorption dips pertaining to the gas being measured. This can be realized at various stages in the interferometer as further discussed. The resulting image signal impinges on one detector half 351, while a n phase stepped image, that has peaks there where no absorption occurs, impinges on the other half 352 of the detector 350.

In particular, according to this embodiment, the relay optics 340 are provided with an interferometric stage 360 combining split beams B, C from splitter 320 into a first image D, and into a second image E at an optical path difference relative to the first image corresponding to half of the central wavelength of the broad band beam, thereby producing first and second images D, E with relative phase differences corresponding to respective on- and off-peak wavelengths relative to the absorption wavelength.

For the Michelson embodiment as disclosed, the interferometric stage 360 has two mirror surfaces 365, 366 positioned relative to a semi-reflective separator interface 367. One of the mirror surfaces is provided with a first reflective portion 365 and a second portion 365' so that split images are projected on said first and second portions of said mirror surface respectively.

Accordingly for said split images, said first and second portions 365, 365' provide the optical path difference corresponding to the half of the central wavelength of the broad band beam. In the disclosed Michelson design about equal optical paths are provided but for a thickness d of glass that is inserted in one of the branches. The image pertaining to that branch will therefore shift backwards by $d*(n-1)/n$. In order to make the other branch to have its image at the exact same focal plane that branch should be shortened by $d*(n-1)/n$.

If the default branches have a length of L, the two branches become, having applied these changes, $$\text{Branch } 1 = L + nd - d$$
$$\text{Branch } 2 = L - \frac{n-1}{n_d}$$

The required optical path difference OPD, the difference between the length of Branch 1 and Branch 2, is found using the same formula that gives the coherence length of the multispectral light, i.e.

$$OPD = \frac{\lambda^2}{\Delta\lambda}$$

Wherein $\lambda$ equals the central wavelength of the band filter and $\Delta\lambda$ equals the spectral separation of the absorption peaks pertaining to the gas being measured.

In the example, the optical path difference is provided by a glass length difference. E.g. the extra OPD is 0.8 mm corresponding to a peak absorption value for $CH_4$ at 1600 nm; is 0.05 mm corresponding to a peak absorption value for NO2 at 440 nm or 8 mm corresponding to a peak absorption value for CO2 at 1570 nm.

This is not essential; in addition or alternatively, the optical path difference may be provided by a differing path length in any refractive medium arranged in one of the split beams before the interferometer mirror, which e.g. may be a combination of differing refractive media. To arrive at an angle insensitive interferometer, the OPD may be a combination of glass and air.

The Michelson type interferometer 360 as depicted has one entrance port 361, and one exit port 362. The mirrors 365, 366 in a Michelson interferometer are positioned perpendicular to the incident beams, which can lead to ghost images due to reflection by the detector surface 351, 352. To overcome this issue the detector 350 may be placed under an angle, e.g. by a wedge 341 such that the light reflected by the detector no longer reaches the mirrors 365, 366 in the interferometer. The Michelson type has an advantageous functionality, size and cost of the interferometer components.

Advantageously, using the telescope is of a telecentric type having a working distance corresponding to the interferometer length measured as optical path length from entrance port to first reflection mirror. For example telecentricity is better than one tenth of a degree. This simplifies imaging of the split images for differing optical distances on the mirror 365.

Alternatively to a Michelson type interferometer a Mach-Zehnder concept can be used. A Mach-Zehnder interferometer has as strong points that it has two entrance ports and two exit ports. This automatically means, based on the conservation of energy, that if one of the exit ports defines the spectral fringes that coincide with the absorption features, that the other exit port receives all the remaining light. In front of the interferometer a band filter has to be used to limit the spectral range to the range where the absorption actually occurs. Light from Earth may then enter the interferometer through one entrance port, while the other entrance port can be used for alignment and calibration purposes.

Figure 4:
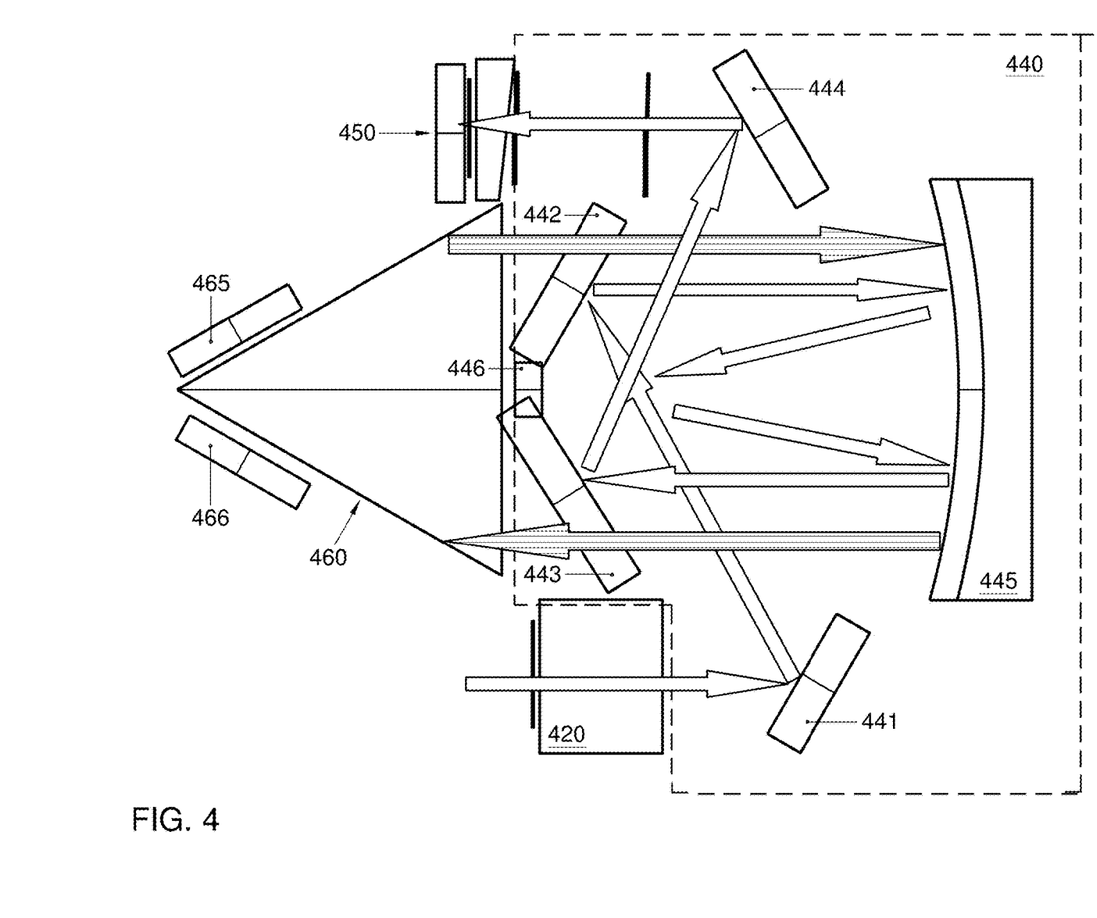
FIG. 4 and FIG. 5 provide detailed design with ray paths.
Figure 5:
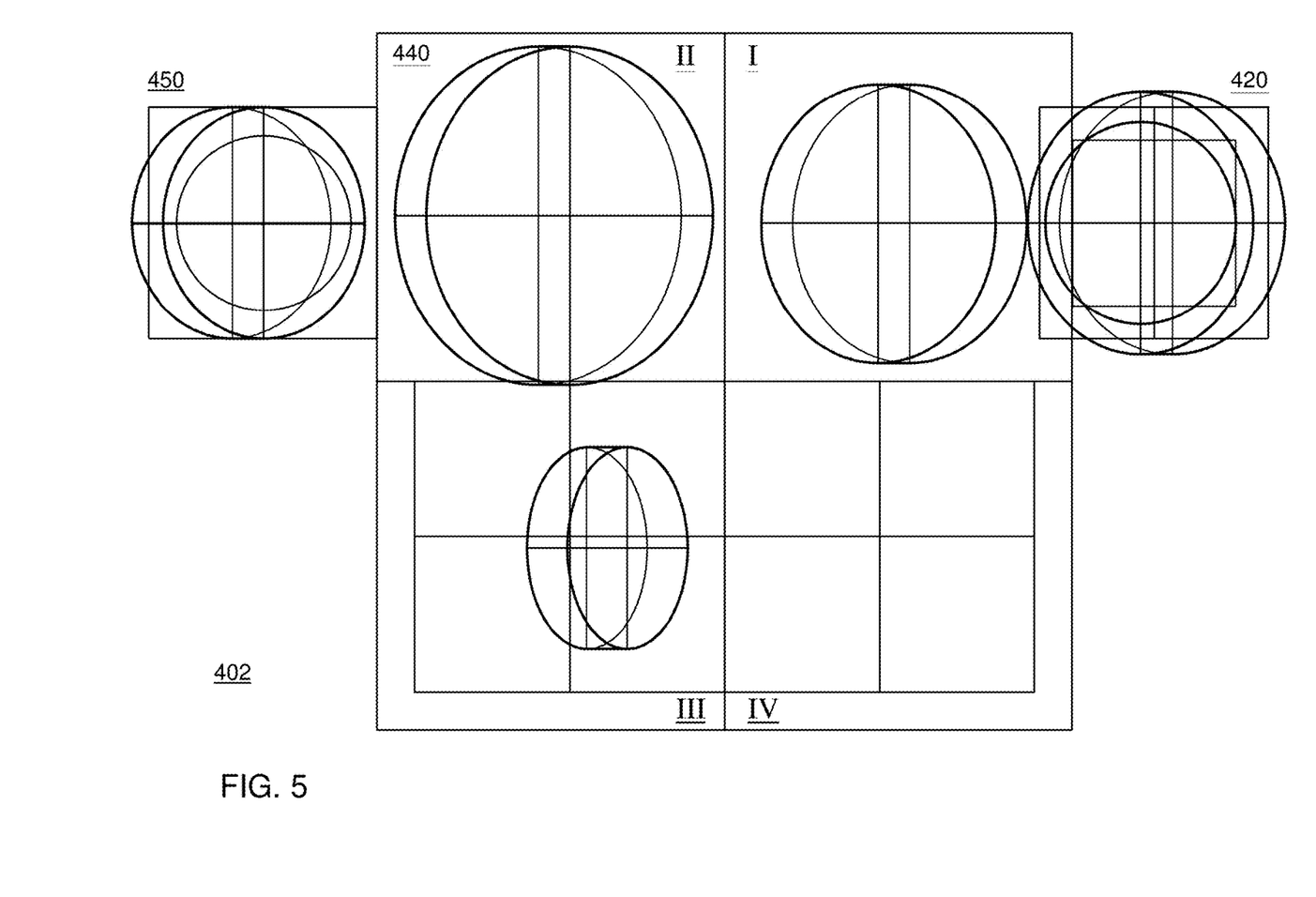

FIG. 4 and FIG. 5 provide a more detailed design 402 with ray paths, for the interferometric stage 460 of a Michaelson type and the imaging/relaying stage 440 include a single Offner imager. FIG. 4 shows the design in top view; FIG. 5 shows the design in front view. The beams of light impinge onto a large Offner mirror 445, coming from the beam splitter 420, in the second quadrant II. The beam exiting the Offner 445 will be in the fourth quadrant IV. Via the Michelson 460 the beam is reflected back from mirror surfaces 465, 466, at least one having reflective portions providing the optical path difference so that split images are projected on said first and second portions of said mirror surface respectively and transferred to the third quadrant III and after passing over the Offner the beam towards the detector 450 is in the first quadrant I depicted in FIG. 4.

FIG. 4 shows the primary mirror 445 being aspheric and secondary mirror 446 being spheric. Splitter 420, detector 450 and first to fourth folding mirrors 441-444 are placed in an upper plane of first and second quadrants I/II and the interferometric stage is placed in a lower plane in third and fourth quadrants III/IV. Primary and secondary mirrors 445, 446 are centred in the quadrants between said planes. In this way a beam entering the splitter 420 is relayed via first and second folding mirrors 441, 442 to the primary mirror 445; backprojected via the secondary mirror 446 onto the primary mirror 445 in the lower plane (quadrants III/IV) and imaged into the interferometric stage 460 in the lower plane. The beam exiting the interferometric stage 460 in the lower plane is projected via the primary 445, secondary 446 to the upper plane, and imaged via third 443 and fourth 444 folding mirrors onto the detector 450.

The splitter/doubler 420 leads to an effective object size, in the example of e.g. 20×20 mm, where field points are tele-centric with an f-number, in the specific embodiment, for example of 18, that is matched to the optical path length in the interferometer stage 460, measured from entrance to mirror surface 465. Since both imaging steps can be done in a 1 to 1 magnification, the relay stage 440 can be provided by a single optic design as disclosed. This advantageously leads to a very compact arrangement of elements. In front of the detector 450 a wedge shaped piece of glass is inserted by which the angles of incidence onto the detector can be changed. The angle may be set to be 50°.

Figure 6:
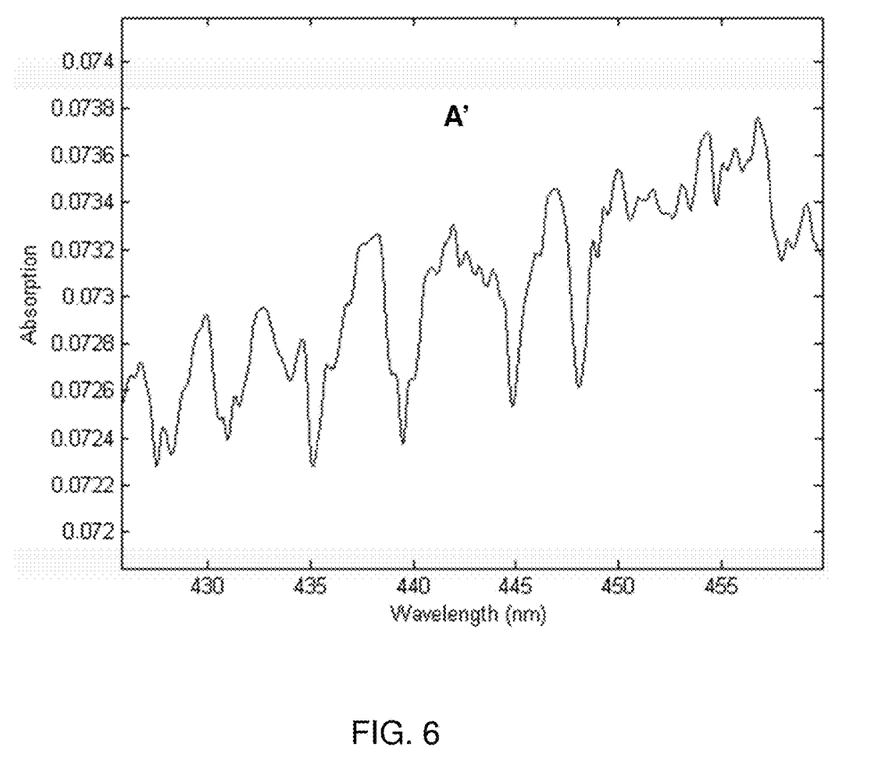
FIG. 6 shows an exemplary chart for measuring absorption strength.

FIG. 6 shows an exemplary chart for measuring absorption strength. Due to wavelength dependent absorption, dips are shown in the absorption spectrum due to NO2 especially around 435, 440, 445 and 450 nm. Corresponding spectra can be found at differing respective wavelengths for e.g. CH4 at 1600 nm, and CO2 at 2000 nm. For this application, e.g. by choosing the optical path difference between the interferometer branches, a spectral interferometric fringe pattern is provided e.g. with $\lambda$ equaling the centre of the absorption band wavelength at 440 nm and $\Delta\lambda$ equals the peaks separation between the absorption peaks, e.g. 3.4 nm. Importantly, the interferometric technique as here disclosed benefits from multiple absorption peaks. It can be calculated that in the case of an absorption strength increase of 1% for each dip in the measured band width, and taking into account that the dips are not all on a regular interval such that only three of the four dips contribute to the signal, the change in signal based on the absorption will be very low, e.g. merely 0.158%.

Illustrative practical values of the signals on the two detector halves will be:

$S1 = 142000 e-/s \cdot px,$ $S2 = 141784 e-/s \cdot px.$

Signal S1 is obtained by one detector half where the intensity is measured from the parts between the absorption peaks. Signal S2 pertains to the intensity in the absorption peaks. Subtracting these two signal and integrating over e.g. 30 s gives a signal of 6476e−/30 s·px, while the summation of the two signals yields 8513520e−/30 s·px. The signal to noise ratio is found to be 2.22/30 s·px. Binning 10×10 pixels will increase the signal to noise ratio by a factor of 10. In GEO-orbit far longer integration times can be taken, e.g. 30 min. A single pixel signal will then already yield a SNR of 17.2. If then the same binning is performed the SNR will be as high as 172 which lead to very accurate measurement results.

Figure 7:
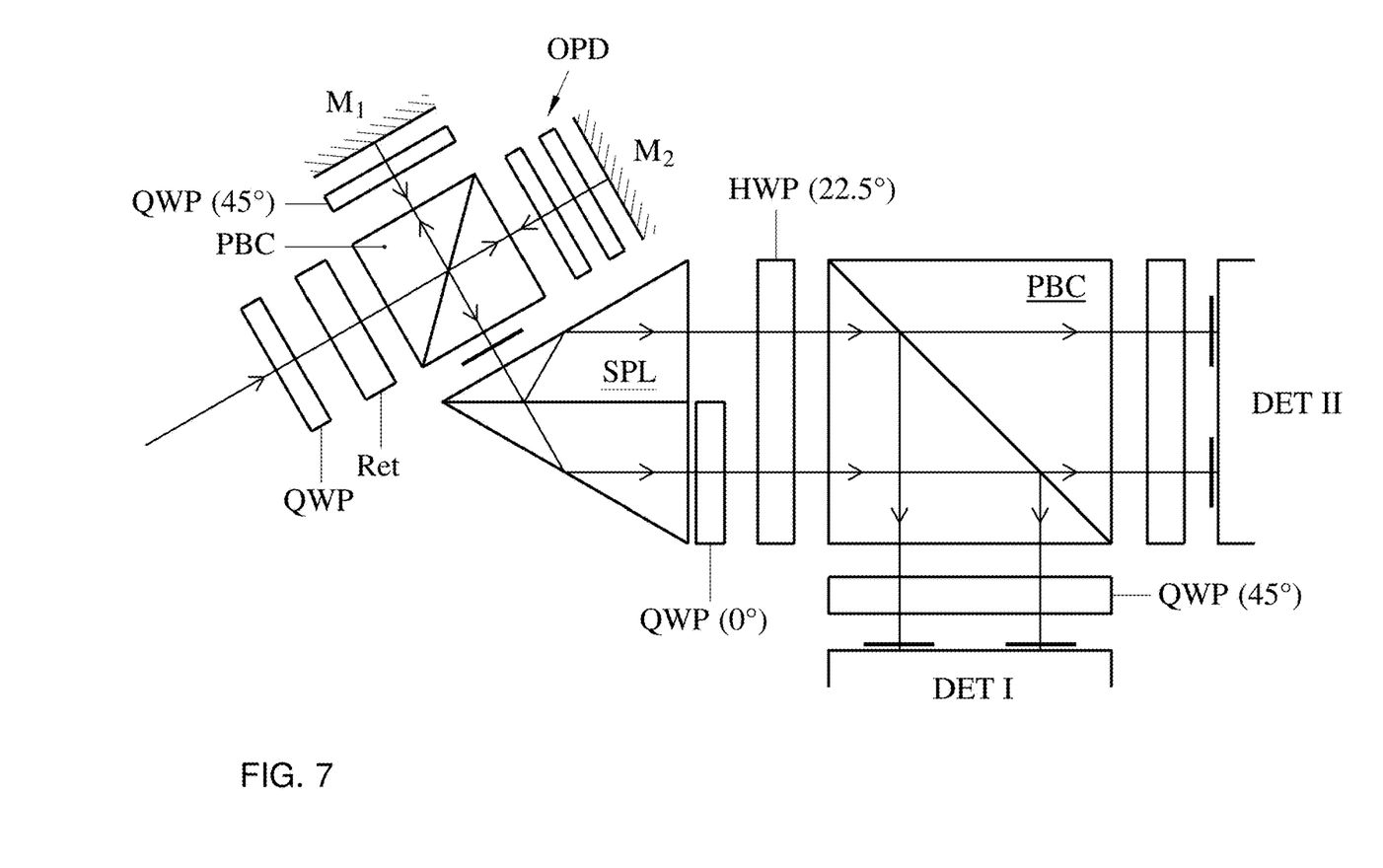
FIG. 7 shows a setup of an aerosol detector.
Figure 8:
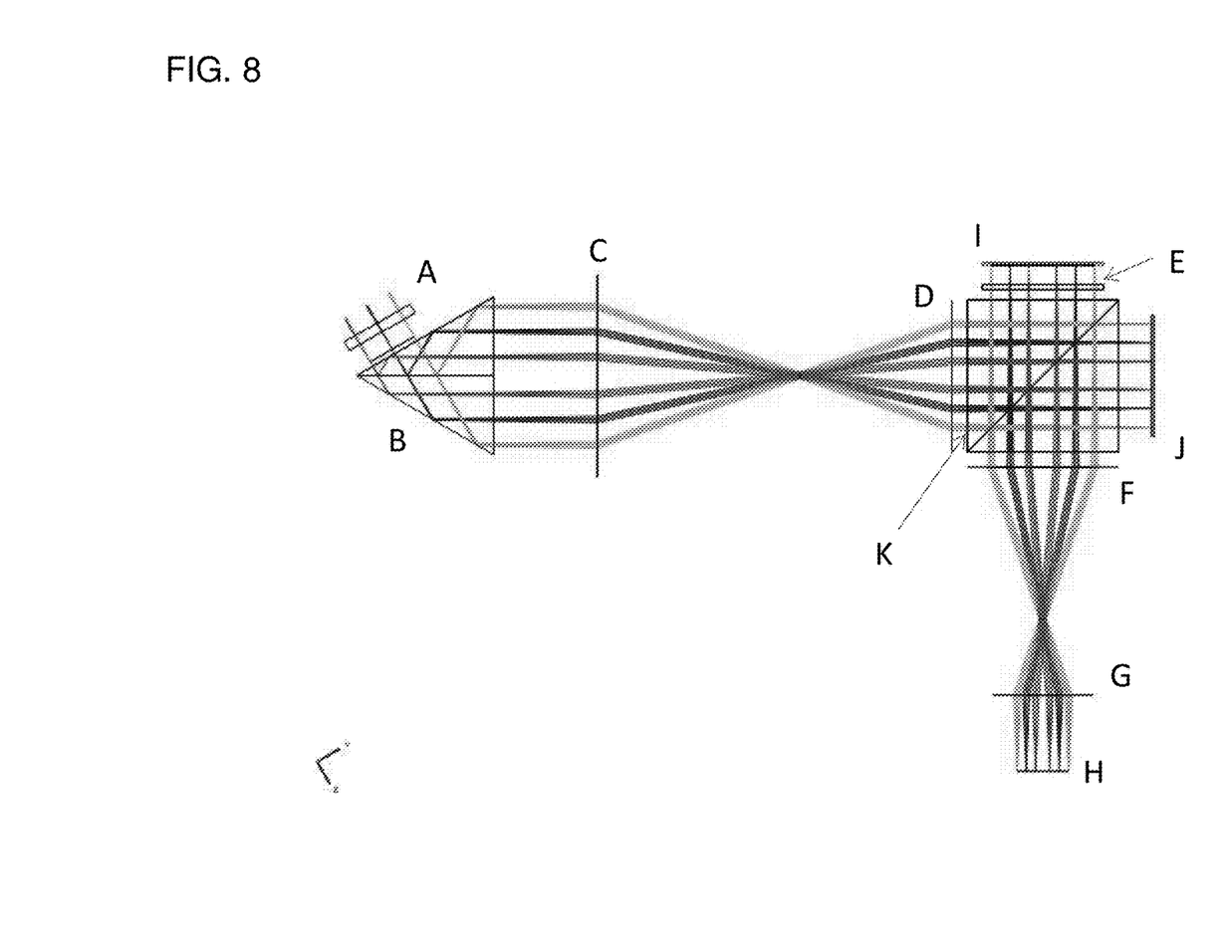
FIG. 8 shows another Michaelson embodiment according to an aspect of the present invention.
Figure 9:
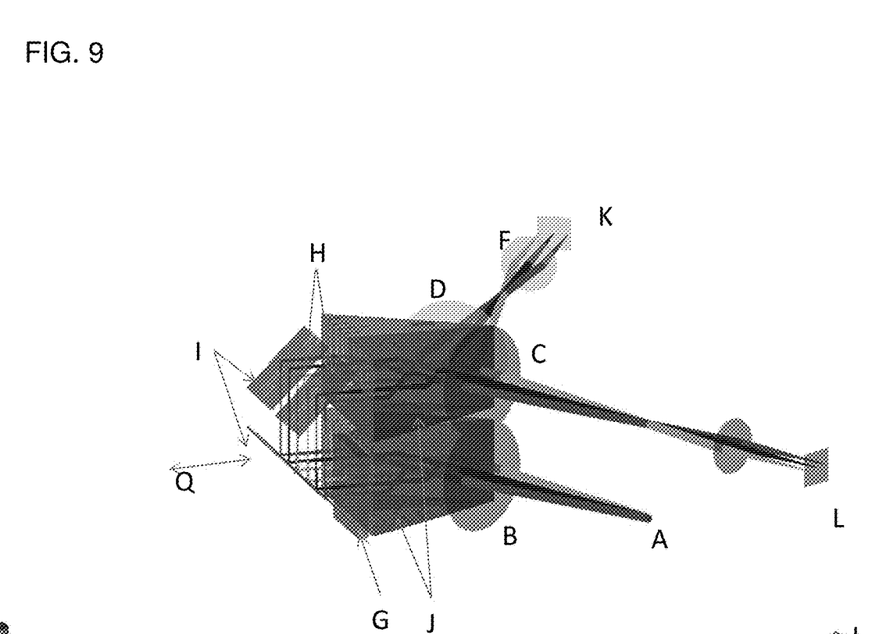
FIGS. 9 and 9A shows another Mach-Zehnder embodiment.
Figure 9A:
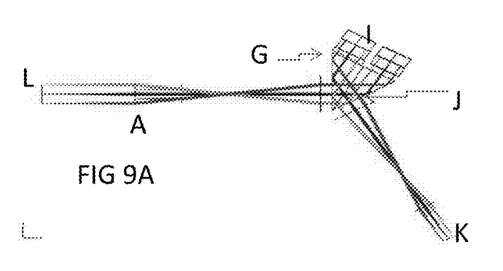

FIG. 7 shows an aerosol detection scheme with a similar interferometric imaging principle. Where in the previous embodiments an image of a spatially resolved absorption corresponding to a gas substance is provided by split images for respective on- and off-peak wavelengths relative to the absorption wavelength, in the present embodiment, a retarder is inserted before the splitter in order to create a phase difference between two orthogonally polarization components that is wavelength dependent. A polarizing beam splitter combines said polarization components at exit ports to produce phase stepped images at different phases. In particular, in the beam path a quarter wave plate is located to transfer linear polarized light into circularly polarized light, followed by the higher order retarder plate. The retarder creates a phase difference between two orthogonally polarisation components that is wavelength dependent. This finally leads to fringes (throughput changing with wavelength) when measured through a polarization filter. The required quarter wave plates can be used to fold the telescope unit to reduce the overall size. The largest field of view may be directed in the flight direction to enable the measurement under a large range of angles on incidence.

The aerosol detection system can be created for all wavelength ranges of interest, provided that the polarization effects in the optical components can be kept within an acceptable range, with a telescope of a refractive type to preserve the polarization states.

In a practical embodiment a polarizing beam splitter cube (PBC) comprises a quarter wave plate (QWP) inserted under 45°. This way of operation makes that all light is being used. The two optical paths in the interferometer are different in air and glass length in order to arrive at an angle independent interferometer with the required optical path difference that is tuned to the wavelength dependent fringe pattern created by the retarder plate. The output are two beams that are co-aligned, where one is s- and the other is p-polarized.

At the entrance of the splitter (SPL) the mutually orthogonally polarized fields are imaged. The beams are 50/50 split within the SPL (no phase issues) after which the split beams I and II are reflected towards the exit of the SPL. The reflection is at an angle larger than the angle of total internal reflection, meaning that 100% of the light is reflected. At the entrance side of the splitter an AR coating is present. The part of the light that is reflected at that side of the SPL, say Part I, obtains a certain phase step δ between the two polarization states. Part II of the light reflex at the side without the AR coating. Here a single layer coating can be created to arrive at a total phase step δ between the two parts equal to 90°. At the exit of the SPL an halve wave plate (HWP) is inserted under 22.5° to align the polarization directions of Part I and Part II to ±45°.

Alternatively, the SPL can be given two identical coatings such that no phase step is introduced within the SPL. Then a standard QWP can be inserted behind one of the exit ports of the SPL (under 0° or 90°) to arrive at the same functionality. The beam combiner is again a PBC with QWP at the exit ports. Each exit ports obtains light from both Part I and Part II, and thanks to the law of conservation of energy, the two outputs have to be 180° out of phase. Side by side in one exit port there are two images, with a 90° phase step between them. In total, four images are obtained on two detectors with phase steps δ equal to 0°, 90°, 180°, and 270°, the standard phase steps for the well-known four bucket phase retrieval algorithm. From these four images the overall intensity can be obtained, as well as the modulation depth (degree of polarization) and the phase (angle of polarization).

In front of the detectors a QWP is inserted to get rid of the reflection of detector. The reflected light is exiting the PBC via the unused entrance port, where it can be trapped.

In a further embodiment illustrated in FIG. 8, another Michaelson type interferometric stage is shown that combines split beams into a first image, and into a second image at an optical path difference relative to the first image corresponding to half of the central wavelength of the broad beam, thereby producing first and second images with relative phase differences. In particular, in the embodiment, a beam splitter/combiner cube K that provides a first image I and a second image J with relative phase differences formed by optical path differentiator E, e.g. a glass plate with a thickness such that the OPD results in a spectral modulation frequency matching the spectral absorption dips in a detection spectrum of a multispectral detection of gas being measured. For this application, e.g. by choosing the optical path difference between the interferometer branches, a spectral interferometric fringe or filter pattern is provided e.g. with A equaling the centre of the absorption band wavelength. The filter pattern matches the absorption dips of the gas, with typical inter peak distances coinciding with the corresponding optical path difference. For the Michaelson embodiment, the beams are combined with a relative phase step of π. To this end, for example, mirror I or J is may be split into two parts where one part provides the π phase step. This phase step corresponds to a spectral fringe that matches either on- or off-peak wavelengths respectively, relative to the absorption wavelength, ensuring that the two images received at H of subsequent mirrors I and J are in counter phase for the absorption wavelength on image plane H.

Prior to the beam cube split images are provided on entrance Lens D by means of splitter B. The light input is restricted by a broad band filter A arranged in the optical beam path before the detector; for transferring a broad band beam with a wavelength spectrum including the absorption wavelength features corresponding to said gas substance. Transfer is provided by lens couples C and D. and F and G This embodiment is preferably combined with a pre stage telescope that has a tele-centric output in order to control the relative phase differences over the beam path, in particular, when traversing optical interfaces in the optical path between input and image plane H.

In a Michaelson type interferometric stage the beams are given a phase shift to arrive at the situation where the two images are complementary in wavelength content, e.g. show on resp off peak spectral responses.

Alternatively, in a Mach-Zehnder type embodiment, such as disclosed in a further embodiment disclosed in FIG. 9 complementary images are obtained on detectors K and L owing to the conservation of energy. In more detail, FIG. 9 discloses an interferometric stage combining said split beams into a first interferometric image K, and into a second interferometric image L at an optical path difference such that the density of the spectral modulation matches the density of the absorption features of the gas being measured, due to optical path differentiator G, e.g. a glass plate with a thickness and refractive index chosen designed to arrive at the required OPD. The two images K and L are π out of phase, meaning that if at one detector the intensity of the spectrum at the absorption dips is being measured, the other detector will automatically get the light of the wavelengths between the absorption dips, thereby producing first and second images with relative phase differences corresponding to respective on- and off-peak wavelengths relative to the absorption wavelength. FIG. 9A provides a schematic plan view of the interferometric embodiment, showing the splitter/combiner parts J, mirrors I and H and optical path differentiator G, detectors K and L, and entrance aperture A. In preceding embodiment the discussion is limited to the functional elements, i.e. most of the powered optics used for imaging has been left out. Practical embodiments may therefor be enhanced by functional features represented by optical elements have the same functional effects.

The invention claimed is:

1. A gas detector system for spatially resolved detection of a gas substance in an area, comprising;

a detector comprising first and second image sensors;

a broad band filter arranged in the optical beam path before the detector; for transferring a broad band beam with a wavelength spectrum including an absorption wavelength peak corresponding to said gas substance;

a telescope, splitter; and relay optics;

wherein the telescope is arranged to imaging the area onto the image sensors; wherein the splitter is arranged to produce split beams; and wherein said relay optics are arranged to relay said split beams respectively to produce first and second images on first and second image sensors; to provide for each pixel of the first image a corresponding pixel of the second image for respective on- and off-peak wavelengths relative to the absorption wavelength and wherein the relay optics are provided with an interferometric stage combining said split beams with an optical path difference into a first image, and into a second image, thereby each image having a spectral fringe pattern corresponding to theoptical path difference that matches absorption dips pertaining to the gas being measured, to produce the first image and second image with a phase difference corresponding to half of the central wavelength of the broad beam, thereby producing said first and second images with relative phase differences corresponding to respective on- and off-peak wavelengths relative to the absorption wavelength; and a controller coupled to the detector, arranged to provide a difference image as a function of the two pixel values of first and second image sensors to produce an image at the spatially resolved absorption wavelength corresponding to said gas substance.

2. The system of claim 1, wherein said interferometric stage having at least two mirror surfaces positioned relative to a semi-reflective separator interface as a Michaelson stage with an optical path difference to produce the spectral fringe pattern; wherein the telescope images said split beams from the splitter onto said mirror surfaces; wherein at least one of the mirror surfaces is provided with a first reflective portion and a second portion so that the split images are projected on said first and second portions of said mirror surface respectively; wherein, for said split images, said first and second portions provide an optical path difference corresponding to half of the central wavelength of the broad band beam.

3. The system of claim 1, comprising a further splitter identical to the first splitter as a Mach Zehnder interferometric stage, that combines said split beams of the first splitter, further comprising a glass plate arranged in an optical path of one of the split beams, to produce the spectral fringe pattern, having at least two detectors positioned relative to a semi-reflective separator interface of the further splitter, said detectors receiving said first and second images respectively.

4. The system of claim 1, wherein the optical path difference producing the spectral fringe pattern is provided by a glass length of 0.8 mm corresponding to a spectral fringe pattern that matches peak absorption values in a spectral range around a central wavelength for CH4 of 1600 nm; is a glass length of 0.05 mm corresponding to a spectral fringe pattern that matches peak absorption values in a spectral range around a central wavelength for NO2 of 440 nm or a glass length of 8 mm corresponding to a spectral fringe pattern that matches peak absorption values in a spectral range around a central wavelength for CO2 of 1570 nm.

5. A gas detector system for spatially resolved detection of a gas substance in an area, comprising;

a detector comprising first and second image sensors;

a broad band filter arranged in the optical beam path before the detector; for transferring a broad band beam with a wavelength spectrum including an absorption wavelength peak corresponding to said gas substance;

a telescope, splitter; and relay optics;

wherein the telescope is arranged to imaging the area onto the image sensors; wherein the splitter is arranged to produce split beams; and wherein said relay optics are arranged to relay said split beams respectively to produce first and second images on first and second image sensors; to provide for each pixel of the first image a corresponding pixel of the second image for respective on- and off-peak wavelengths relative to the absorption wavelength; and wherein the relay optics are provided with an interferometric stage combining said split beams with an optical path difference into a first image, and into a second image, thereby each image having a spectral fringe pattern corresponding to the optical path difference that matches absorption dips pertaining to the gas being measured, to produce the first image and second image with a phase difference corresponding to half of the central wavelength of the broad beam, thereby producing said first and second images with relative phase differences corresponding to respective on- and off-peak wavelengths relative to the absorption wavelength a controller coupled to the detector, arranged to provide a difference image as a function of the two pixel values of first and second image sensors to produce an image at the spatially resolved absorption wavelength corresponding to said gas substance; and wherein the telescope is of a telecentric type having a working distance corresponding to the interferometer length.

6. The system of claim 1, wherein a wedge block is provided in front of the detector by which the angles of incidence onto the detector can be changed to prevent backreflection.

7. The system of claim 1, wherein the interferometric stage is of a Michaelson type and the relay optics include a single Offner imager.

8. The system according to claim 7, wherein the imager is formed by a primary mirror being aspheric; and a secondary mirror being spheric; and first to fourth folding mirrors; wherein splitter, detector and first to fourth folding mirrors are placed in an upper plane and the interferometric stage is placed in a lower plane, said primary and secondary mirrors being centered between said planes; in such a way that a beam entering the splitter is relayed via first and second folding mirrors to the primary mirror; backprojected via the secondary mirror onto the primary mirror in the lower plane and imaged into the interferometric stage in the lower plane; the beam exiting the interferometric stage in the lower plane and projected via the primary, secondary to the upper plane, and imaged via third and fourth folding mirrors onto the detector.

* * * * *